United States Patent [19]

Rose et al.

[11] Patent Number: 5,734,588
[45] Date of Patent: Mar. 31, 1998

[54] BORE PROBE FOR TUBE INSPECTION WITH GUIDED WAVES AND METHOD THEREFOR

[75] Inventors: Joseph L. Rose, State College; John J. Ditri, Philadelphia, both of Pa.; Frank T. Carr, Juiter, Fla.; Jack C. Spanner, Jr., Charlotte, N.C.; Dale Jiao, Wynnewood, Pa.

[73] Assignee: Electric Power Research Institute Inc., Palo Alto, Calif.

[21] Appl. No.: 669,699

[22] Filed: Jun. 24, 1996

Related U.S. Application Data

[63] Continuation-in-part of Ser. No. 372,679, Jan. 17, 1995, abandoned.

[51] Int. Cl.$^6$ ............................. G01N 29/04; G01N 29/12
[52] U.S. Cl. ........................... 364/507; 73/644; 364/506
[58] Field of Search ........................... 73/642, 643, 644; 364/506, 507

[56] References Cited

U.S. PATENT DOCUMENTS

| | | | |
|---|---|---|---|
| H924 | 6/1991 | Chimenti | 73/644 |
| 3,417,609 | 12/1968 | Graham | 73/642 X |
| 3,736,044 | 5/1973 | Lean et al. | 359/305 |
| 3,806,840 | 4/1974 | Whitney et al. | 333/145 |
| 4,100,809 | 7/1978 | Bobrov et al. | 73/638 |
| 4,309,905 | 1/1982 | Maizenberg et al. | 73/643 |
| 4,893,496 | 1/1990 | Bau et al. | 73/32 A |
| 5,072,427 | 12/1991 | Knowles | 367/118 |
| 5,159,838 | 11/1992 | Lynnworth | 73/644 |
| 5,162,618 | 11/1992 | Knowles | 178/18 |
| 5,179,862 | 1/1993 | Lynnworth | 73/861.28 |
| 5,629,485 | 5/1997 | Rose et al. | 73/599 |

OTHER PUBLICATIONS

Ditri et al.; "Generation of Guided Waves In Hollow Cylinders By Wedge and Comb Type Transducers"; Review of Progress in Quantitative Nondestructive Evaluation, vol. 12, pp. 211–218, 1993.

Viktorov; "Rayleigh and Lamb Waves"; Plemun Press New York; pp. 6–11, 82–85, 123–127 & 132–137, 1967.

Article entitled "A Novel Guided Ultrasonic Wave Technique for Tubing Inspection Efficiency", by J.J. Ditri, J.L. Rose, F. T. Carr and W.J. McKnight, Proceedings of the 11th International Conference on NDE in the Nuclear and Pressure Vessel Industries, Albuquerque, N.M., 30 Apr.–2,May, pp. 49–54.

Artitle entitled "Excitation of Guided Elastic Wave Modes in Hollow Cylinders by John J. Ditri and Joseph L. Rose", J. Appl. Phys. 72(7), 1 Oct. 1992, pp. 2589–2597.

Article entitle "Utilization Oblique Incidence in Acousto–Ultrasonics", by A. Pilarski, J. L. Rose, K. Balasubramaniam, J. Da–Le, Proceedings of the Acousto–Ultrasonics: Theory and Application, Blacksburg, VA, Jul. 12–15, 1987, pp. 1–10 and drawings.

*Primary Examiner*—Edward R. Cosimano
*Attorney, Agent, or Firm*—Flehr Hohbach Test Albritton & Herbert LLP

[57] ABSTRACT

Guided ultrasonic waves are used for the detection of defective tubes in a heat exchanger or steam generator by using a transducer which generates a guided wave at predetermined parameters of phase velocity and frequency to operate at a point on a dispersion curve which minimizes leakage of ultrasonic energy to fluid surrounding the tube. Various techniques of generating ultrasonic waves of various phase velocities such as a comb type filter allow phase velocity points on a dispersion curve to be freely selected.

13 Claims, 17 Drawing Sheets

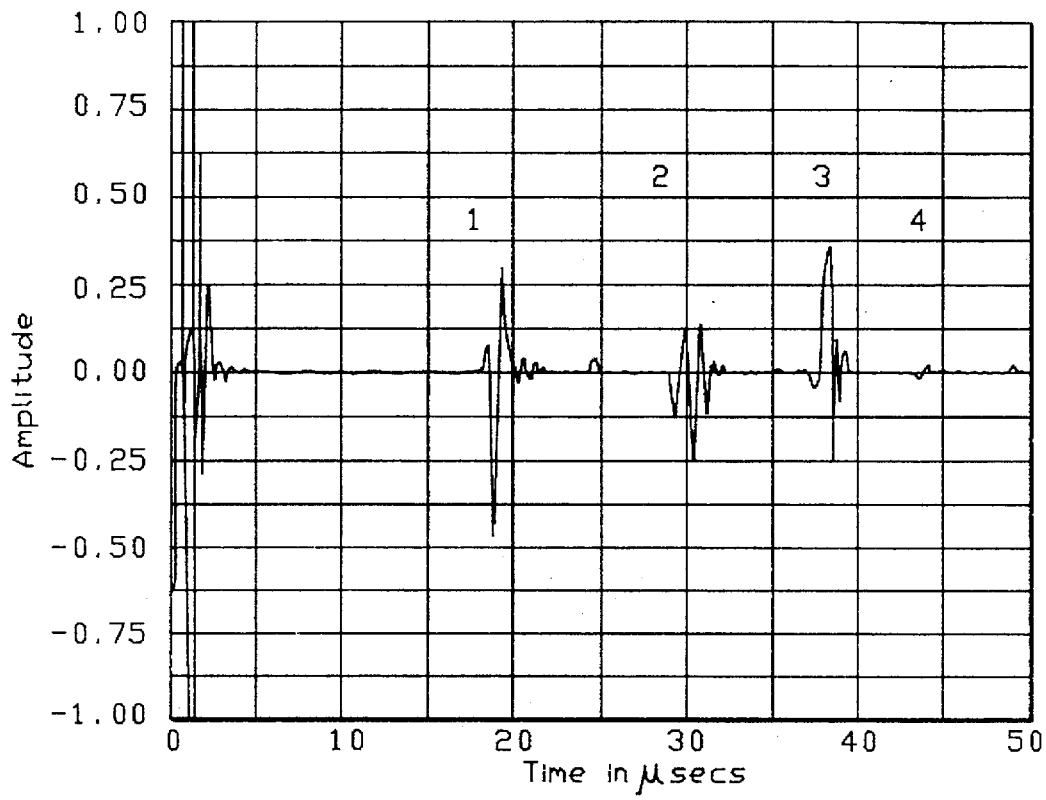
FIG.5A  FREE
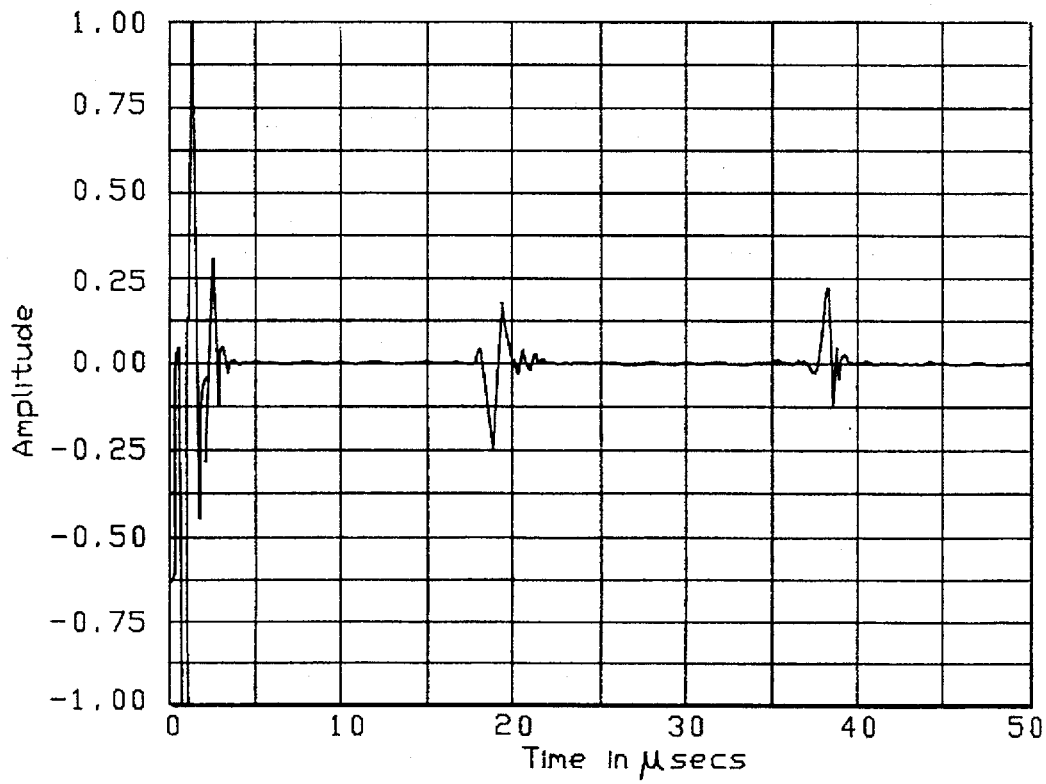
FIG.5B  WATER LOADED

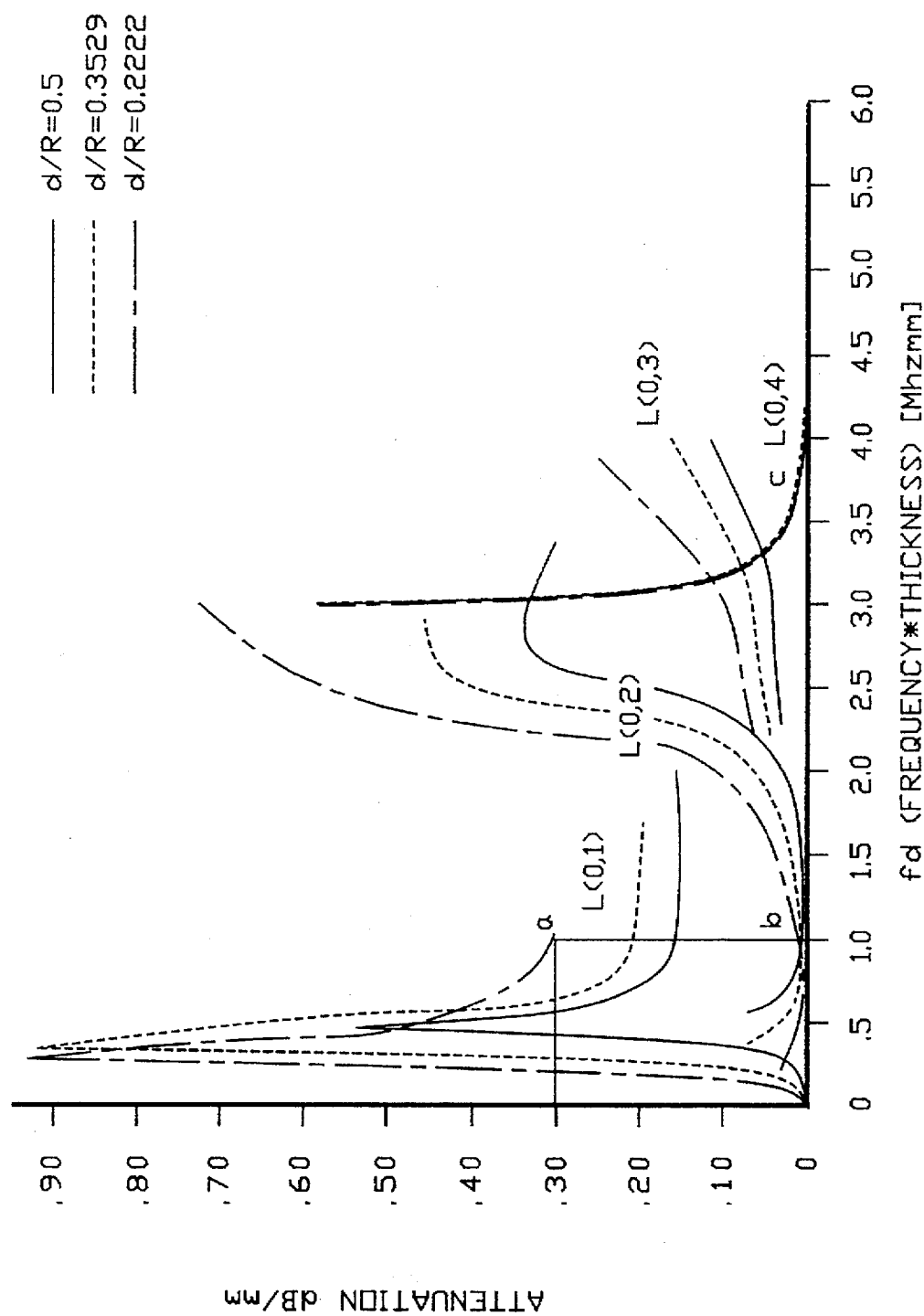

BORE PROBE FOR TUBE INSPECTION WITH GUIDED WAVES AND METHOD THEREFOR

This is a continuation-in-part of application Ser. No. 08/372,679, filed Jan. 17, 1995 and now abandoned.

The present invention is directed to a method using a bore probe for tube inspection with guided waves and more specifically where the guided waves are ultrasonic and are used for sensing defects in heat exchanger and steam generator tubing.

BACKGROUND OF THE INVENTION

The use of guided ultrasonic waves for the nondestructive evaluation of tubing is well known. Other than inspect on a point-by-point basis, procedures which are commonly used in normal beam ultrasonics utilize the signal response (echo) of such waves. For example, in an article entitled "A Novel Guided Ultrasonic Guided Wave Technique for Improved Tubing Inspection Efficiency", Proceedings of the 11th International Conference on NDE in the Nuclear and Pressure Vessel Industries, Albuquerque, N. Mex., 30 Apr.–2 May, 1992, pp. 49–54, the use of guided waves to inspect an entire length of tubing of several meters is discussed, including a generation technique using as an ultrasonic radiator a conically shaped piezoelectric element housed in a plexiglass enclosure which is used as a probe which is inserted in the end of a tube.

Unfortunately the science behind guided wave technology is very complex which has hindered the commercial use of such probes in ultrasonic nondestructive evaluation. And such technique is needed because of America's aging power generation infrastructure where it is now necessary to be able to efficiently inspect all types of tubing and types of materials. Of particular concern today is the thousands of miles of heat exchanger and steam generator tubing.

OBJECT AND SUMMARY OF INVENTION

It is a general object of the present invention to provide an improved method of using a bore probe for tube inspection with guided waves, and also apparatus therefor.

In accordance with the above, there is provided a method of using guided ultrasonic waves for inspection of defects in heat exchanger and steam generator tubing using a transducer for generating the guided waves at predetermined parameters of phase velocity, $C_{ph}$, and frequency, f, to operate at a point on a dispersion curve of a specific ultrasonic guided wave mode within the tubing. Such point minimizes leakage of ultrasonic energy to fluid surrounding such tube and provides good longitudinal penetration. The phase velocity and frequency are chosen by the following steps:

determining the tube material properties and thickness, d;

generating dispersion curves of $C_{ph}$ versus fd for a plurality of ultrasonic modes;

from such curves determining attenuation versus fd;

and selecting points of substantially zero or minimal attenuation on the curves and determining the the frequency and phase velocity of such selected points and utilizing such determined frequency and phase velocity as the predetermined parameters for generating a guided wave.

In addition there is provided both apparatus and method of generating guided waves by providing a transducer with spaced ultrasonic radiators, the spacing being proportional to the specific phase velocity which is required for a desired point on a dispersion curve.

BRIEF DESCRIPTION OF DRAWINGS

FIGS. 5A and 5B show the echo reflections of ultrasonic waves in a tube.

FIG. 7 is another form of the characteristic dispersion curves of FIG. 6 showing having attenuation rather than phase velocity as in axis.

DETAILED DESCRIPTION OF PREFERRED EMBODIMENTS

Figure 1:
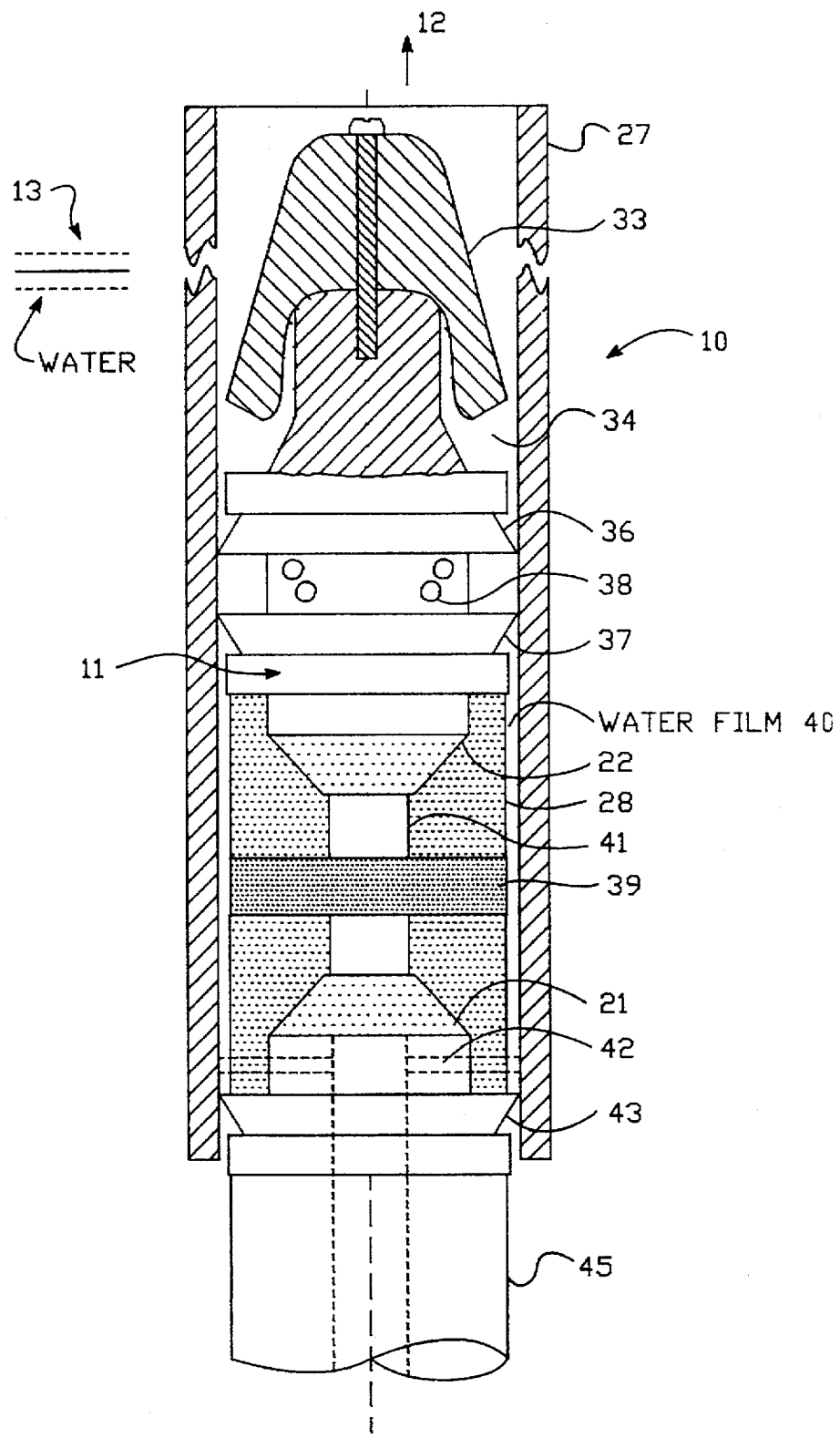
FIG. 1 is a cross-sectional view of a bore probe inserted in a typical tube employing the apparatus of the invention.

FIG. 1 is a schematic cross-sectional view steam generator tubing 10 having a bore probe 11 inserted in the tube which is capable of generating guided ultrasonic waves down the tube in the direction indicated by the arrow 12. As will be discussed below, such guided waves travel several meters in order to provide a reflective wave which indicates defects as well as other anomalous conditions in the tube. Other information which may be gained may also be defect or flaw classification and sizing analysis. This is all achieved by the use of a fixed probe 11 in the end of tube 10 which after insertion need not be moved during inspection and/or rotated. Normally as indicated at 13, tube 10 is a steam generator or heat exchanger tube which would be immersed in water. And then as will be discussed below, as more specifically shown in FIG. 4, such water will cause the guided waves 15 which occur in the thickness, "d" of the tube wall 27 to leak most of their energy, as shown by the arrows 16, into the surrounding water. This, of course, causes severe attenuation and limits the penetration distance of a guided ultrasonic wave for purposes of defect detection. Still referring to FIG. 4, the distance down the tube is the Z distance, the thickness of the tube wall is designated, d; the inner radius is "a", the outer radius is "b", and the radius and angle Θ relationships are indicated.

Referring back to FIG. 1, the ultrasonic bore probe radiator device 11 includes a first conical piezoelectric element 21 and a oppositely mounted conical piezoelectric element 22; one is used for transmitting an ultrasonic guided wave down the tube and the other for receiving.

Figure 2:
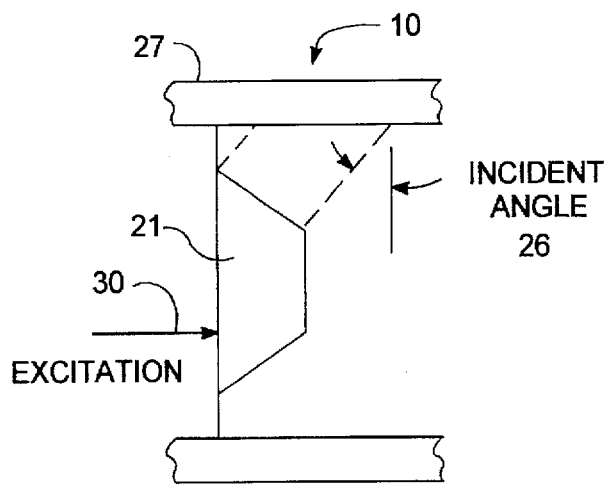
FIG. 2 is a detailed cross-sectional view of a portion of FIG. 1 showing the operation of the invention.

FIG. 2 illustrates the details of a typical element 21 within the tube 10 where the sloped or conical side of the transducer 21 forms an incident angle 26 with the tube wall 27 whose SINE function according to Snell's law, is directly proportional to the phase velocity $C_{ph}$, of the ultrasonic guided wave down the tube. Snell's law stated in words is that the incident angle 26 is equal to the arc sine of the ratio of the phase velocity of the longitudinal wave in the plexiglass housing 28 (see FIG. 1) in which element 21 is encased and the phase velocity of the guided wave down the tube. Thus it is apparent that by adjustment of the incident angle 26, phase velocity may be adjusted.

As illustrated, radiator 21 generates the desired radially symmetric waves. However, a preferred form of radiator is a truncated conical piezo-composite shell which has ceramic elements embedded in epoxy. This is commercially available from Kraukramer Branson Company of Lewistown, Pa., Product Code 389-001-900, Model BPDU, 3.5 MHz, Dual Conical Elements.

Figure 3:
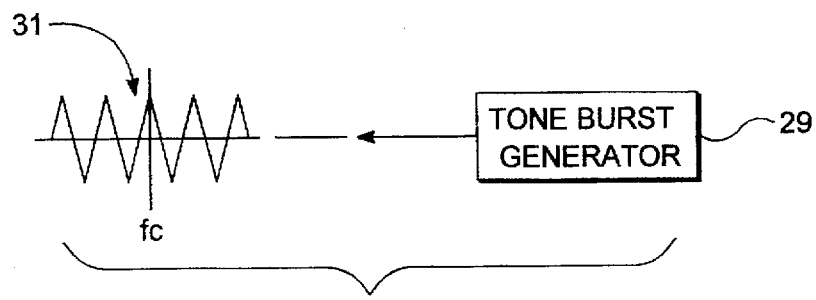
FIG. 3 is a circuit schematic of and associated wave forms of a device used in the present invention.

The excitation to the piezoelectric radiator 21 is indicated at 30 and is provided as shown in FIG. 3 by a tone burst generator 29. Such generator generates a center frequency, $f_c$, with a typical range of frequencies of 5 to 10 megahertz. Then by varying the small number of cycles, e.g., 10 to 20, in the tone burst 31, the desired effective bandwidth excitation signal may be optimized. In operation, the conical piezoelectric transducers 21 and 22 provide generation or reception of an angled beam which provides almost all the possible modes of ultrasonic generation which could exist in the tube and, in addition, typically the wave generated is in a radially symmetric longitudinal mode. Since the incidence of the ultrasonic wave is symmetric; it is independent of the angle Θ (see FIG. 4). The above article entitled "A Novel Guided Wave Technique for Improved Tubing Inspection Efficiency" discloses such possibilities.

Again referring to FIG. 1, the remaining structure of the ultrasonic radiator includes at its forward end a centering guide 33 with semiflexible fingers attached to a buffer unit 34 which in turn is attached to a first water seal unit 36. There is a second water seal unit 37 which in conjunction with a third water seal unit 43 retains the plexiglass housing 28 for the two ultrasonic radiator elements 21 and 22. Connecting seal elements 36 and 37 are water outlet ports 38. Plexiglass housing 28 is separated from the tube wall 27 by a thin film 40 of water. Then at ultrasonic radiators 21 and 22 is copper tubing and cables and water drain 41. An acoustic barrier 39 isolates the two ultrasonic radiators. Water inlet ports are provided. Finally wand 45 provides a coupling tube to electronic frequency generating and analyzing devices and in general for analysis of the wave structure of the reflected echo, which as well as location provides other information as to sizing and type of the defect.

FIG. 5A shows the echo waveforms, for a tube which is not immersed in water, and FIG. 5B for a tube which is water loaded. The horizontal axis is the time of the reflection in microseconds and the vertical the resultant amplitude of the echo which is detected by, for example, the element 22 of FIG. 1. The generated wave occurs at zero time and then as shown in FIG. 5A there are four reflections designated 1, 2, 3 and 4. As FIG. 5B illustrates, because of water loading, the waves 2 and 4 disappear because of the "leakage" caused by the water loading. This concerns a concept of the present invention which will be discussed below.

Figure 4:
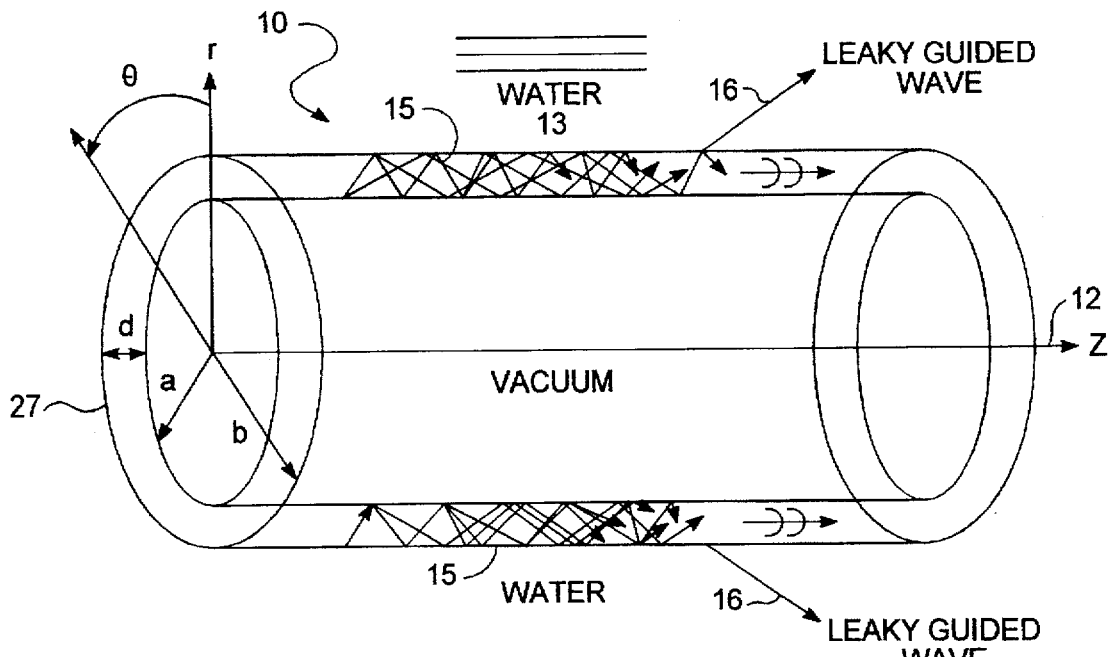
FIG. 4 is a perspective view of ultrasonic waves in a tube illustrating the operation of the invention.
Figure 6:
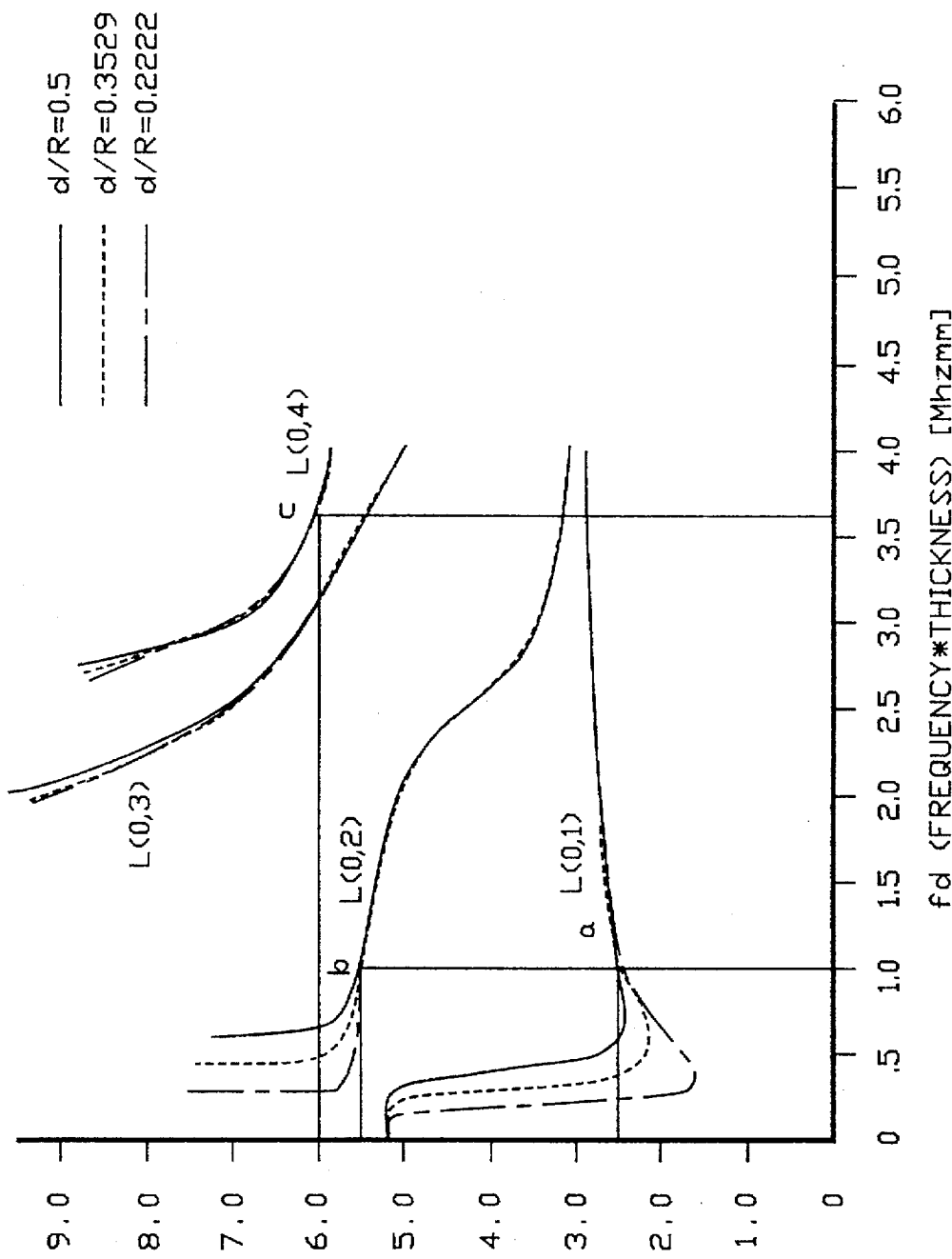
FIG. 6 are characteristic dispersion curves illustrating the present invention of phase velocity versus frequency× thickness.
Figures 23, 24:
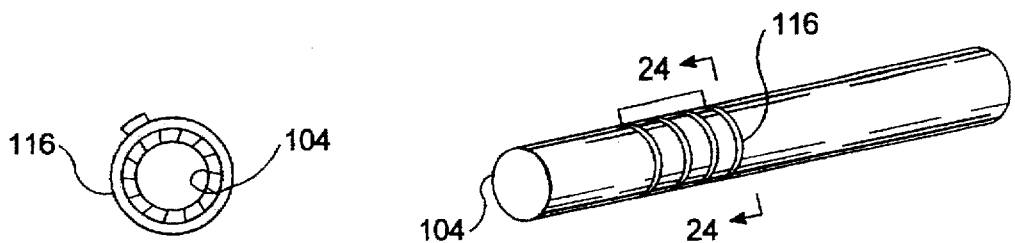
FIG. 23 is a perspective view of a 360° comb transducer.
FIG. 24 is a simplified cross-sectional view taken along line 24—24 of FIG. 23.
Figure 25A:
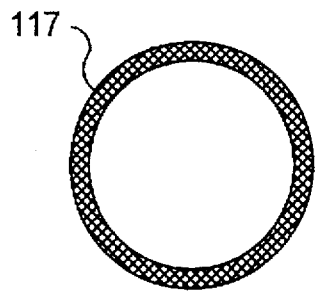
FIGS. 25A through 25C show various cross-sectional views of one type of comb transducer illustrated in FIG. 23.
Figure 26A:
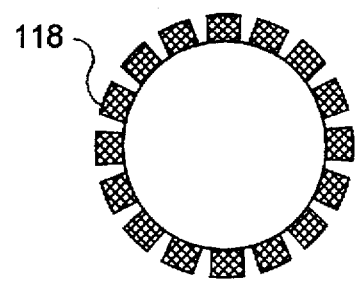
FIGS. 26A, 26B and 26C are various cross-sectional view showing another type of comb transducer of FIG. 23.
Figure 32:
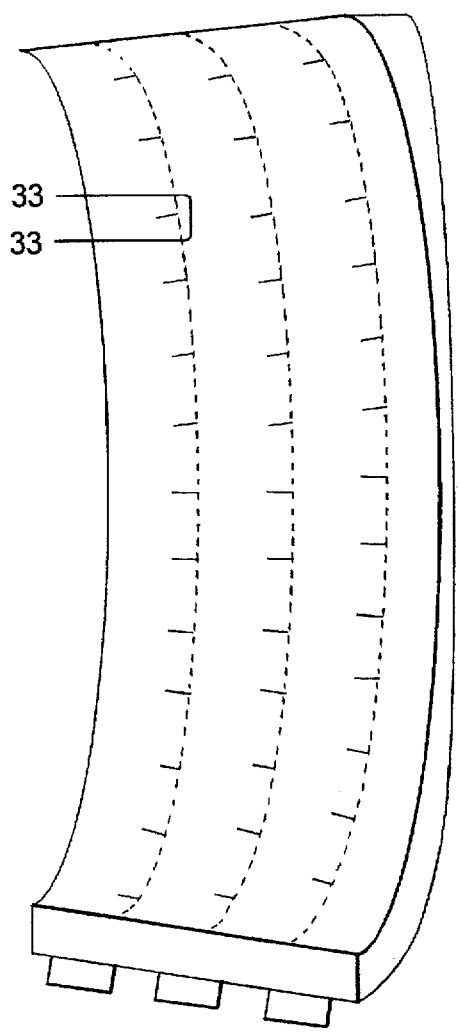
FIG. 32 illustrates a perspective view of a wrap-around comb type transducer.
Figure 33:
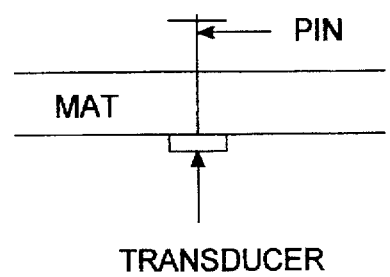
FIG. 33 is a detailed simplified view of a portion of FIG. 32 taken substantially along line 33—33.

FIGS. 6 and 7 illustrate dispersion curves which have been theoretically generated for a steel tube 10 such as shown in FIG. 4 which has the various ratios of thickness dimension d and radius R as illustrated in the drawing. The dispersion curve for each ratio is analysis unless non-axisymmetric phase propagation is thoroughly understood. This is important since reflection from a defect is generally non-axisymmetric. In most practical situations, axisymmetric modes are recommended. One way of exciting the axisymmetric modes is to use a 360° comb transducer that consists of a group of circular transducers 116 that are equally spaced arranged in parallel in pipe axial directions as illustrated in FIG. 23 and FIG. 24. See also FIGS. 32 and 33 showing another type of wraparound transducer. Because of the even excitation around the circumference, only axisymmetric modes can be generated. The 360° transducer can be made in two ways as illustrated in FIGS. 25A, 25B, 25C and 26A, 26B and 26C that show the cross-section of the 360° comb transducer. FIG. 25A is the 360° comb transducer that consists of a group of single circular elements 117 which work together in phase. This type of transducer should generate uniform axisymmetric modes in the pipe. But it may be used only for pipes of one particular diameter. FIG. 26A shows the elements 118 of the 360° multiple array comb transducer. Each 360° element consists of a group of equally spaced normal beam transducers, called a transducer array. This type of transducer can be used on pipes of similar diameters by adjusting the normal beam transucer spacing.

Figure 25B:
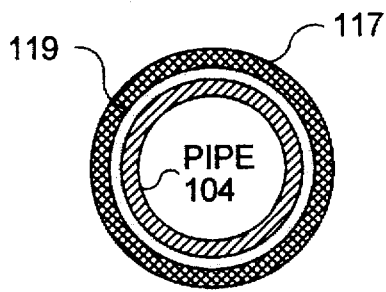
Figure 26B:
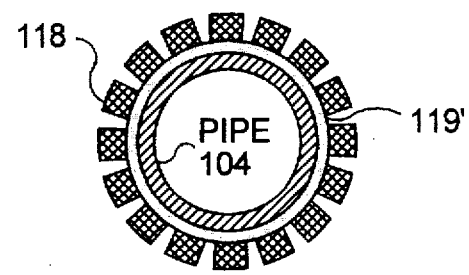
Figure 25C:
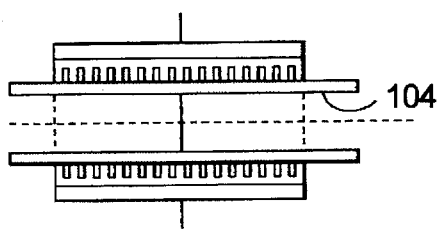
Figure 26C:
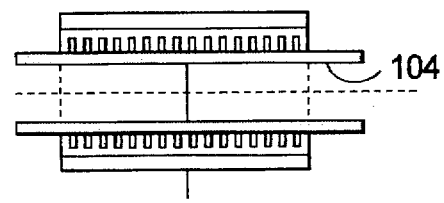

Referring to the details of the one-piece transducer 117 in FIG. 25A, as illustrated in FIG. 25B, the pipe or tube 104 which is the inner diameter has overlaid on it a shoe 119 on which is, of course, the single transducer 117. Then, referring to FIG. 26B, there is a similar shoe 119' but affixed to it are individual transducers 228. Then, FIGS. 25C and 26C show axial cross-sections.

Figure 8A:
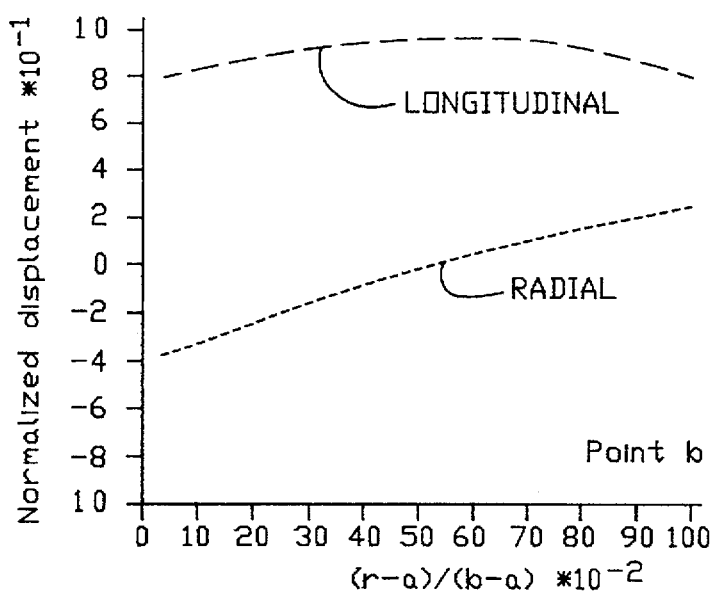
FIGS. 8A, 8B and 8C are curves showing the wave structure of both radial displacement and longitudinal displacement across the thickness of a tube at three points of interest on the dispersion curve of FIGS. 6 and 7.
Figure 8B:
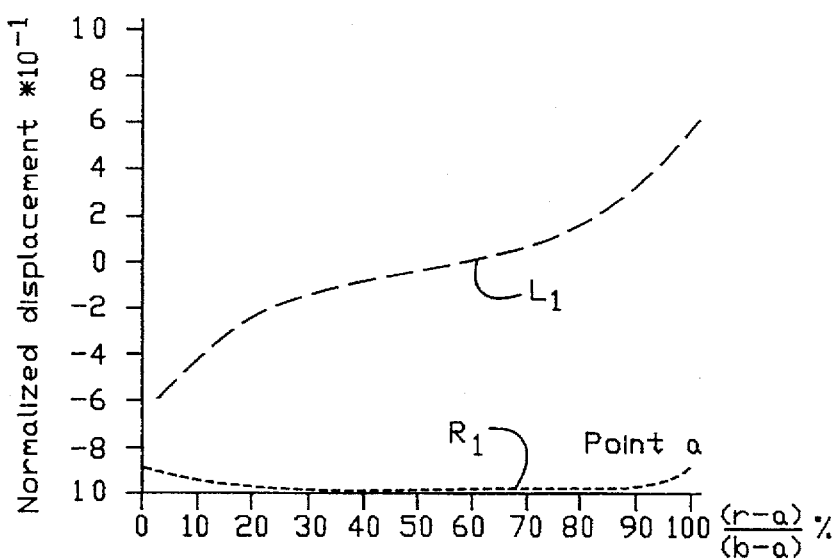
Figure 8C:
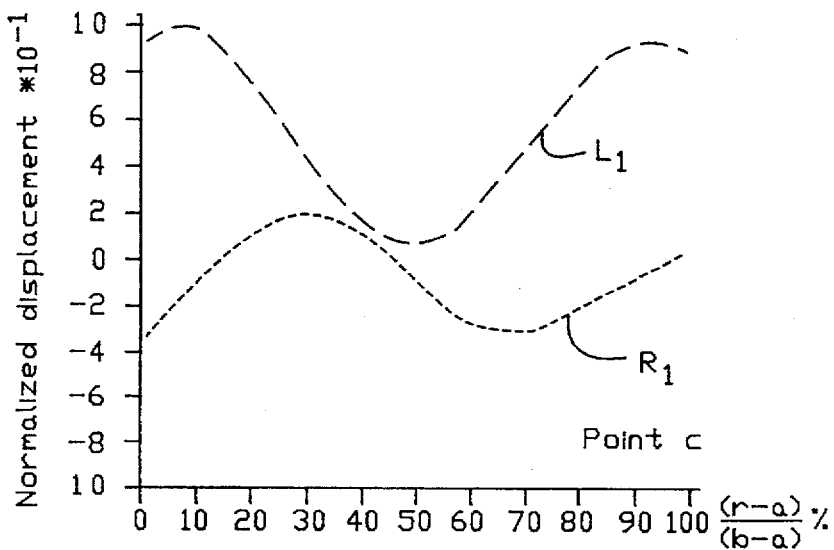
Figure 27A:
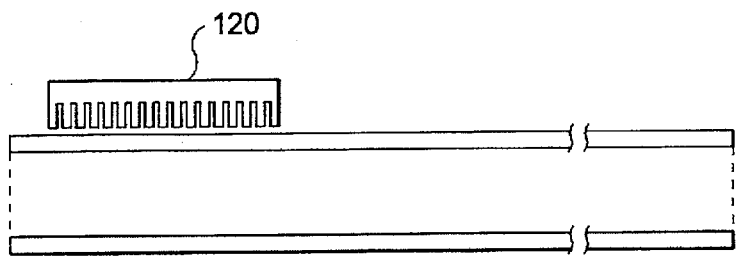
FIGS. 27A, 27B and 27C illustrate various combinations of a comb transducer and receiver for sensing defects in the associated pipe.
Figure 27B:
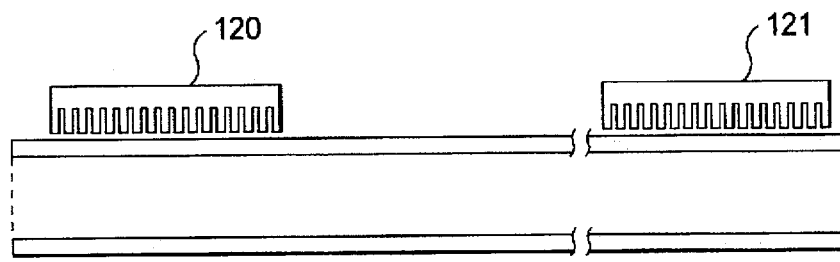
Figure 27C:
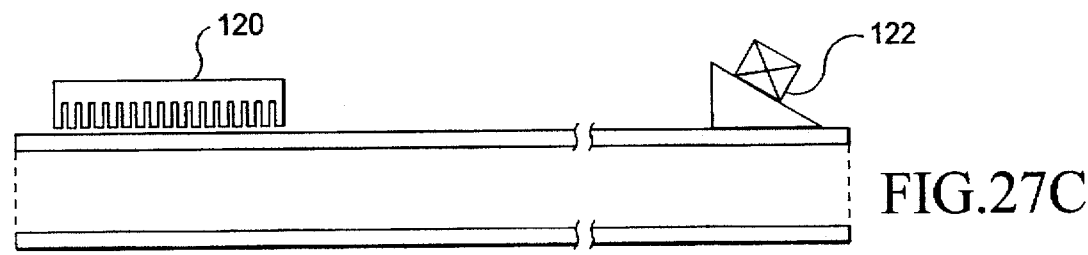

The generated guided wave in the pipe or plate may be received using three methods as illustrated in FIGS. 27A–27C. FIG. 27A is the pulse echo method: the comb transducer 120 example, at point c for a phase velocity of 6 mm per microsecond and an fd product of 3.7 Mhzmm, no leakage of ultrasonic energy occurs if a tube is water loaded on the outside surface. On the other hand, at point a, there is significant and severe water leakage. The foregoing is further illustrated in the displacement curves of FIGS. 8A, 8B and 8C where the points b, a and c are respectively illustrated. These curves show the radial and longitudinal displacement distributions across the thickness of the tube at the three points of special interest a, b and c. The vertical axis of these curves is normalized displacement and the horizontal axis is "0" for the inside wall with the outside wall surface at "100" location. For the points b and c (FIGS. 8A and 8C), the radial or R displacement is close to zero at the outside wall surface "100"; thus, they are conducive to no energy loss into the fluid if the tube were fluid loaded on the outside surface. Longitudinal displacement shown by the other "L" curves is still substantial for crack detection on either the outside or inside surface. The displacement curves are generated by using a standard wave structure analysis from well known formulas in elasticity as, for example, shown in the following references: 1) S. P. Timoshenko and J. N. Goodier, "Theory of Elasticity", 3d Edition, McGraw-Hill, New York, 1973, 2) D. C. Gazis, "Three Dimensional Investigation of the Propagation of Waves in Hollow Hollow Circular Cylinders I; Analytical Foundation", The Journal of the Acoustical Society of American, Vol. 31(5), pp 568–578, May 1959. Such curves are also shown in the publication "Ultrasonic Guided Wave Inspection Concepts for Steam Generator Tubing", Materials Evaluation, Vol. 2, No. 2, February 1994, pp. 307–311.

In summary, because of the radial displacement in a particular mode which is close to zero at the outside surface of its waveguide (tube 10), there is consequently no energy interaction and interface between the waveguide and outside wall. This means that the radial power flow of point c is independent of water loading and thus propagates long distances without being severely attenuated. In comparison, point a (FIG. 8B) because of the significant radial displacement at the outside surface (see R curve), point a loses its ultrasonic energy drastically.

Figure 9:
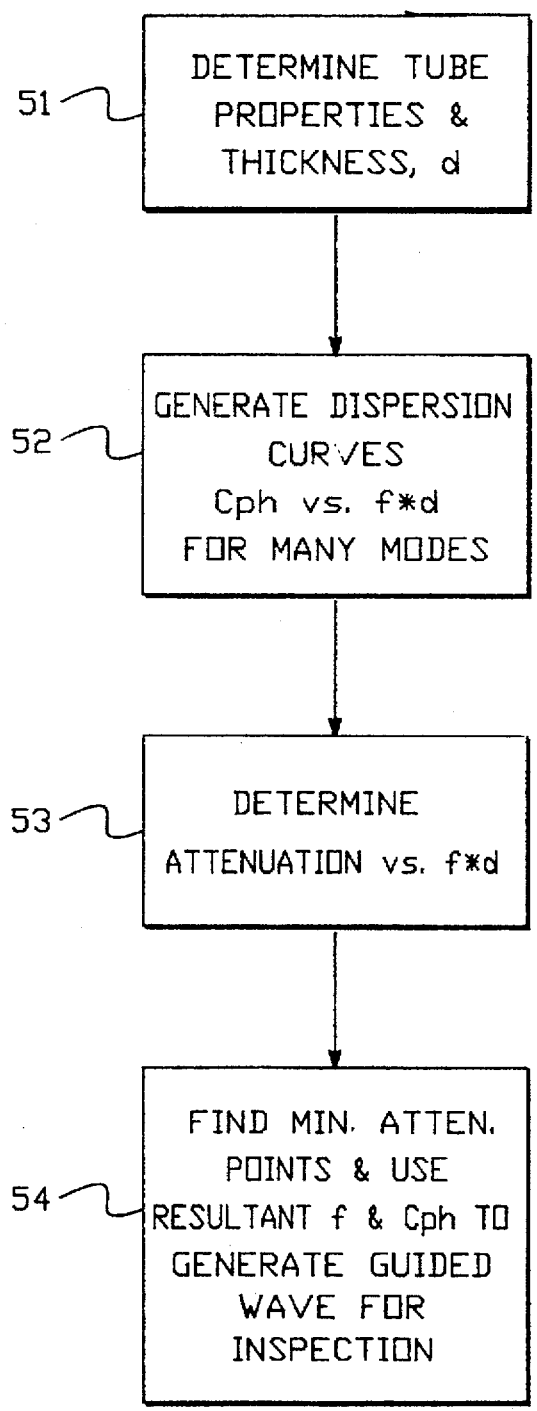
FIG. 9 is a flow chart illustrating the process of the present invention.

Thus the method of the present invention may be summarized with reference to FIG. 9, where to implement it, the following steps are illustrated. First in step 51, the properties of the tube and thickness must be determined, and then in step 52 dispersion curves of $C_{ph}$ vs. f*d are generated for many modes. And in step 53, the attenuation versus f*d is determined for each mode. As an equivalent to this step the radial displacement curves which contain equivalent information may also be utilized. In step 54, the minimum attenuation points are found. The resulting frequency and phase velocities derived from the curves of FIGS. 6 and 7 may be utilized to generate an effective ultrasonic guided wave for tube inspection. To choose the proper phase velocity, in one embodiment of the invention, the angle of incidence of the conical radiator may be varied in utilizing Snell's law.

Figure 10:
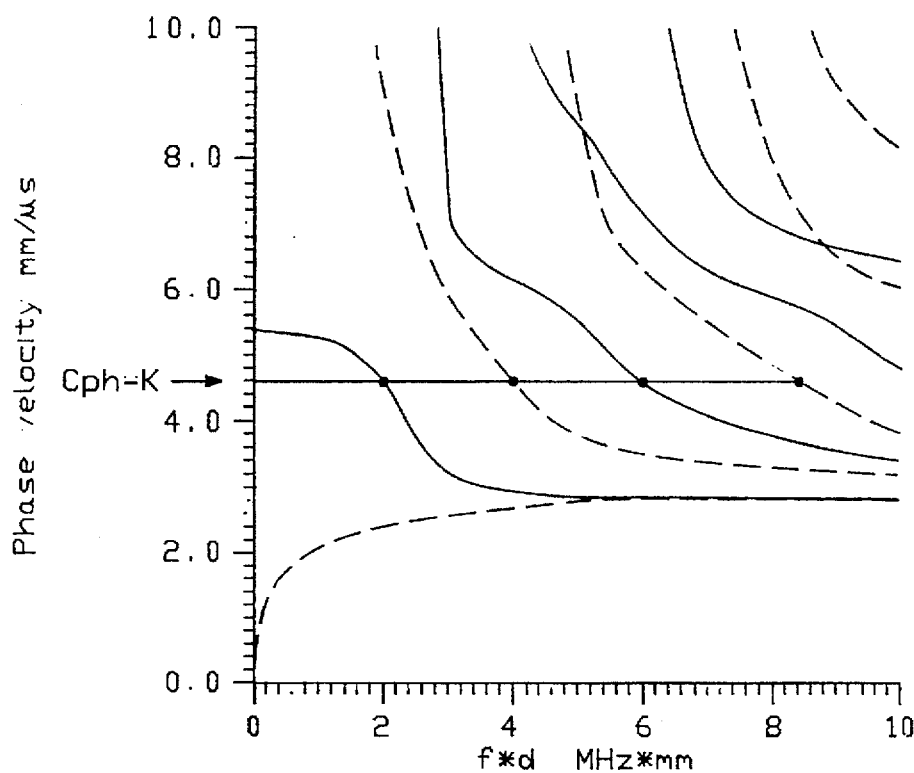
FIG. 10 is a set of dispersion curves illustrating the operation of one embodiment of the invention.

Referring to FIG. 10, which is another set of dispersion curves where phase velocity is held constant. Then frequency may be shifted and all the points occur on a horizontal line. This illustrates that with a fixed conical angle radiator as illustrated in one embodiment, as shown in FIG. 2, that as illustrated in the drawing of FIG. 10, there are only four possible excitation points. Referring to Snell's law, by way of that law, and a fixed angle of incidence for a conical radiator of the type shown in FIG. 2, only that one particular value of phase velocity becomes possible. Unfortunately, these four points of choice may not be the four points of choice with respect to optimized penetration power for defect detection, classification and sizing.

Figure 11A:
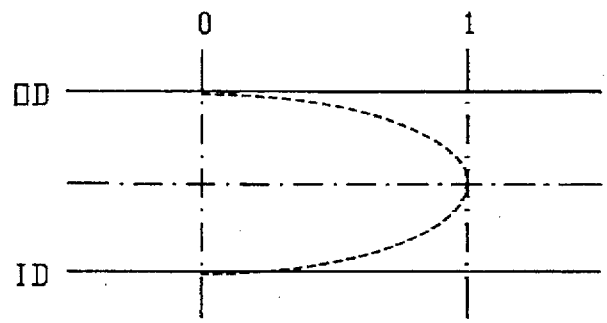
FIGS. 11A through 11D illustrate possible wave structure patterns across the thickness of the tubing.
Figure 11B:
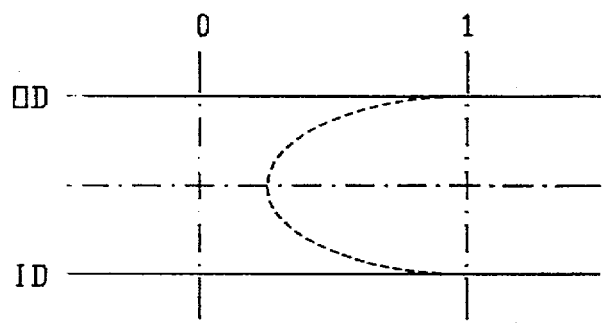
Figure 11C:
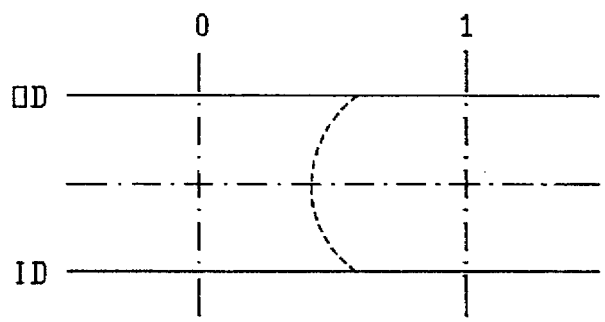
Figure 11D:
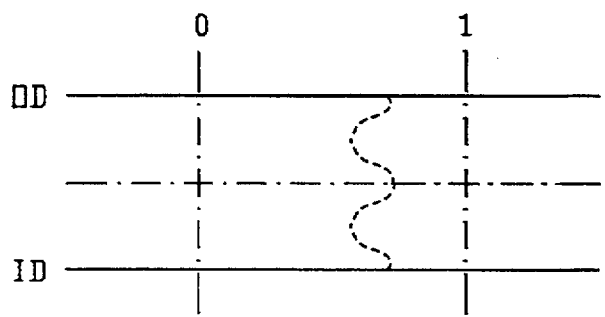

An optimization parameter of principal concern is the wave structure across the thickness of the cylindrical tubing as discussed above. This wave structure will relate to the longitudinal or radial displacement components shown in FIGS. 11A through 11D. Here a series of four different wave structure possibilities for either the longitudinal or radial displacement component is illustrated. If one wave structure is chosen, a particular phase velocity value must be chosen. The two optimal configurations shown are for FIGS. 11A and 11B. A displacement value on the outside surface of the tube in 11A is practically zero whereas in 11B it is a maximum value. In FIGS. 11C and 11D are shown intermediate possibilities for unusual variations. If tubing is located under water, it is desirable to have the radial displacement component on the outside surface of the tube to be almost zero. On the other hand, with respect to the detection of defects on the outside surface of the tube, if these are of critical importance, the longitudinal or radial displacement components should be of maximum value at the outside surfaces as in 11B. Then, again with respect to FIG. 11A, if there are fins on the outside of the tube, the pattern of 11A might be most useful since this response would be relatively insensitive to items contained on the outside surface.

Figure 12:
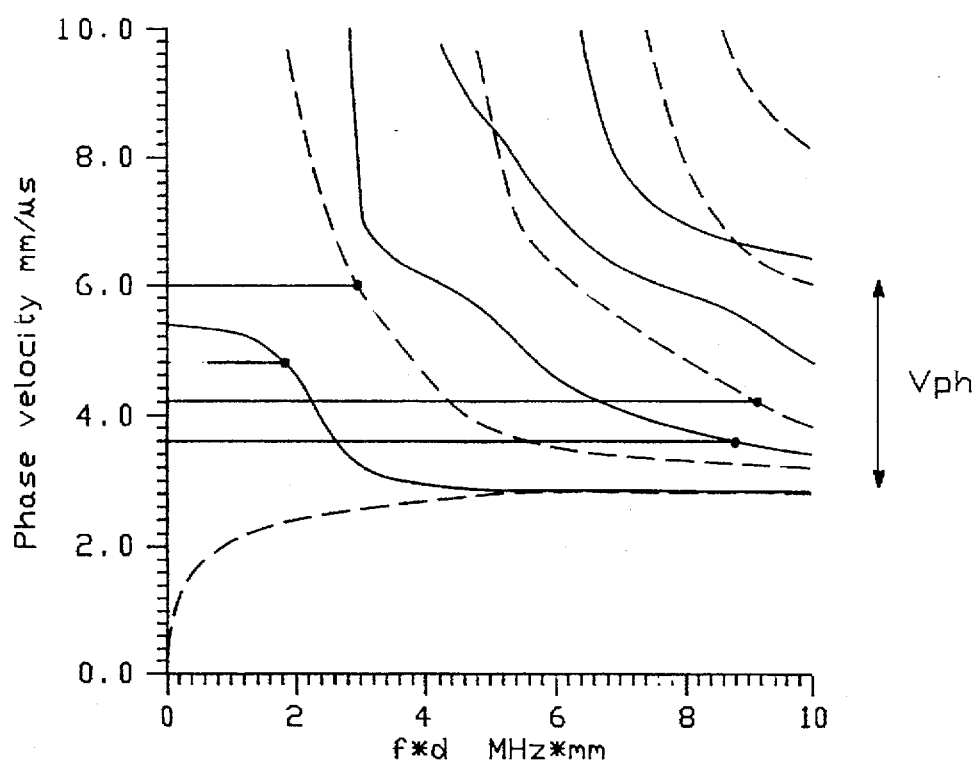
FIG. 12 illustrates a set of curves similar to the dispersion curves of FIG. 10 but illustrates another embodiment of the invention.

Thus it is desirable to be able to produce a variety of different specified points on a dispersion curve such as illustrated in FIG. 12. Here where both phase velocity and frequency may be freely varied, there is an unlimited selection of points. Because of this unlimited selection, points can be selected from any points on the modes illustrated in the dispersion diagram of FIG. 12 with respect to desired wave structure across the thickness of the tubing, optimized for defect detection, classification, or sizing.

Figure 13A:
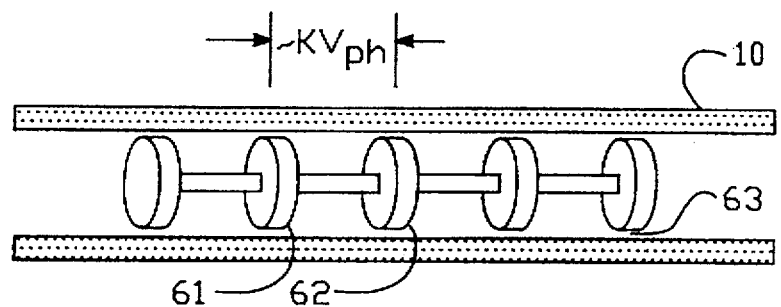
FIGS. 13A, 13B and 13C are cross-sectional diagrammatic views illustrating another embodiment of an ultrasonic radiator in accordance with the present invention.
Figure 13B:
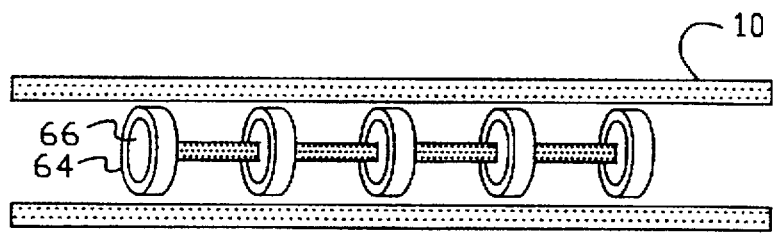
Figure 13C:
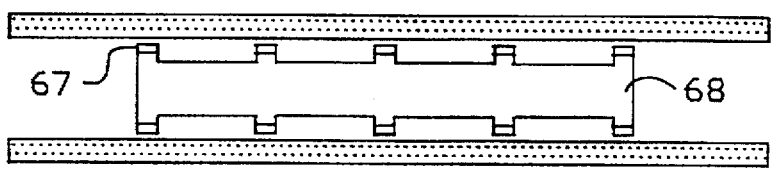

To provide this flexibility, FIGS. 13A, 13B, and 13C show three different comb type ultrasonic radiators for producing uniform radial excitation over 360° where the spacing between the elements is related to the phase velocity value that is selected. Thus referring to FIG. 12, almost any point may be freely selected for generation of an optimum guided wave. Thus in FIG. 13A the spacing between the piezoelectric discs 61 and 62 is shown to be proportional to phase velocity. This disc is a solid piezoelectric disc which has a thin fluent couplant 63 within the tube 10. FIG. 13B shows piezoelectric element 64 wrapped over a solid disc 66. FIG. 13C illustrates piezoelectric elements 67 wrapped over a solid or cylindrical stepped rod 68. Frequency tuning may be accomplished by the tone burst generator of FIG. 3.

Figure 14:
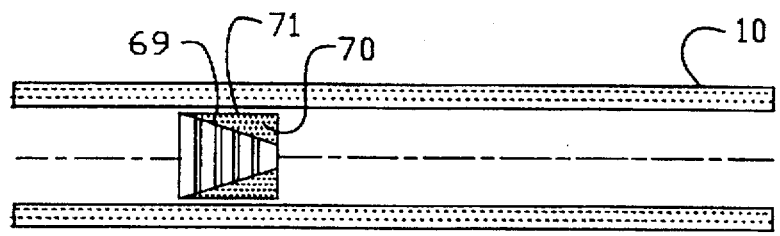
FIG. 14 is another embodiment of an ultrasonic radiator.

FIG. 14 illustrates another conical wave structure similar to that of FIG. 2 but with an annular array 69 encased in plexiglass 70 with a coupling to the tube 10 by a thin fluid couplant 71. Here flexibility is provided for an effective beam angle change and thus a phase velocity change by providing a time delay profile from one element to another. This changes the effective incident angle and thus the phase velocity. Six or seven elements 69 are sufficient for achieving a reasonable phase velocity and frequency choice. Change of time delay may be done by spacing as illustrated in FIG. 7 or by electronic phasing means with respect to tone burst generator 29.

Figure 15:
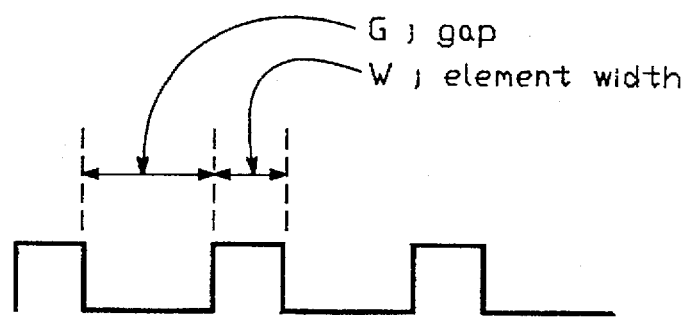
FIG. 15 shows a technique for computing phase velocity for the ultrasonic radiators of FIGS. 13A through 13C.
Figure 16:
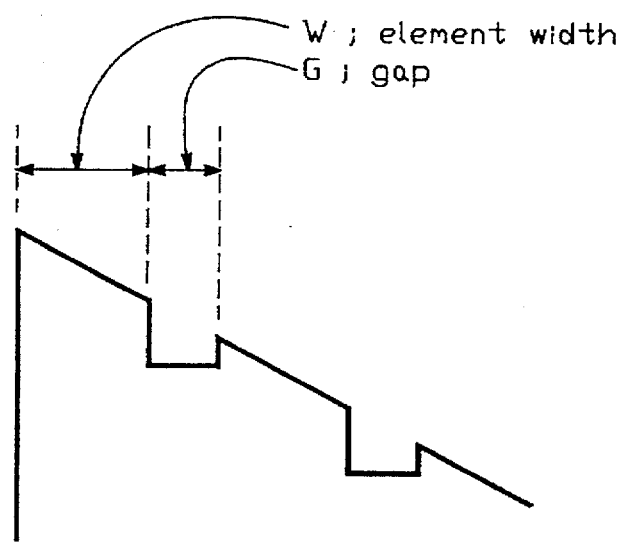
FIG. 16 illustrates the technique of computing phase velocity for the ultrasonic radiator of FIG. 14.

FIG. 15 illustrates spacing of the comb type filters between gap and element width. With the comb arrangement the gap is very large compared to the element width itself. In contrast with the conical annular ray of FIG. 16, the gap should be as small as possible.

Figure 17:
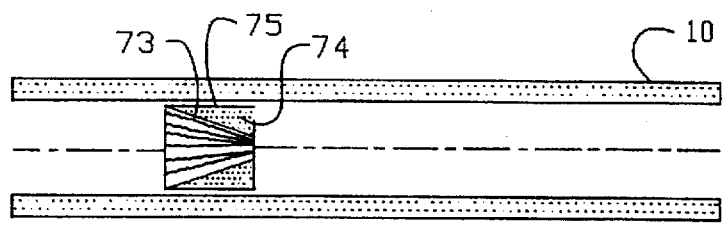
FIG. 17 is a cross-sectional view of a type of ultrasonic receiver of the present invention.

FIG. 17 illustrates a transducer receiver which has a conical element 73 encased in plexiglass 74 with a thin fluid couplant 75. Segments of the conical element 73 are longitudinal.

Figure 18:
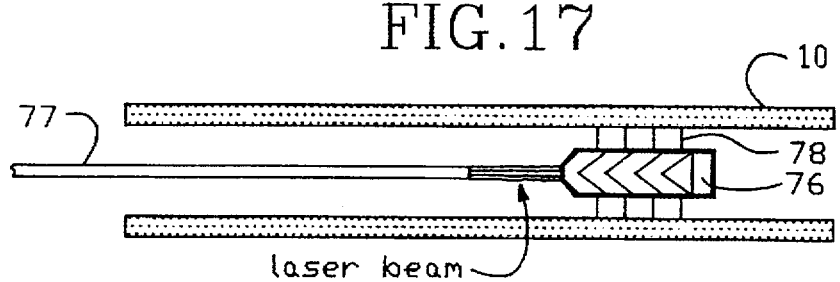
FIG. 18 is a cross-sectional view of another ultrasonic radiator of the present invention.

FIG. 18 is an alternative technique of achieving the comb type excitation of FIGS. 13A, 13B and 13C including beam splitting device 76 excited by lasers through an optic cable 77. The beam is split into a series of laser beams 78 which strike at various paths on the tube 10. Specific gap distances and time delay profiles are used to obtain the phase velocity and frequency values of choice.

Thus far the comb-type transducers of FIGS. 13–18 have been illustrated as being internal to the tube or pipe being tested for defects. However, by placing a comb transducer on the exterior of the tube the flexibility and scope of the technique of the present invention can be enlarged for inspection of defects of all types of pipes, such as heating pipes, chemical gas and fluid convey-type, etc. This is done by the comb transducer generating the guided waves at predetermined parameters, phase velocity and frequency to operate on a point of a dispersion curve of a specific ultrasonic guided wave mode within the pipe. And such a point is chosen to optimize the sensitivity to the defects and also penetration capability as discussed above with relation to the other types of transducers. However, the use of comb transducers of the various designs, to be discussed below, have the following advantages.

(1) Plate waves may be generated in pipes of a variety of materials even in materials of low phase velocities where angle beam techniques do not work. (It should be mentioned that such angle beam techniques include, for example, mounting a longitudinal wave transducer on a Plexiglass angle beam shoe to send a longitudinal wave into the Plexiglass shoe which then generates guided waves in the plate or pipe. This has several limitations including the high profile which make installation difficult and the angle beam technique which generates guided waves by Snell's Law is not able to produce guided waves in lower phase velocity materials; in addition, in hot environments its efficiency is degraded.)

2. The present comb transducer can be designed to generate wave modes at any desired points on the dispersion curves; therefore, the best wave mode with a suitable wave structure can be selected and generated for any particular problem, hence giving optimal sensitivity to a certain defect as well as penetration capability if needed.

3. There is more efficient penetration potential since no shoes are required; hence, there is no loss in Plexiglass shoes as discussed in the prior art.

4. A higher frequency mode generation is possible for increased resolution.

5. A transducer may be of a smaller size for small area inspection. The low profile comb transducer can be mounted on more components that call for smaller sizes because of poor access.

6. It is suitable for high temperature pipe inspection and this can be done by use of a metal comb shoe.

7. Pure modes can be generated since all of the energy is in phase as it enters the pipe structure.

From a very specific standpoint, comb transducer designs follow the following steps:

1. Determine the pipe material properties and dimensions, inner and outer diameters and wall thickness, d.

2. Mathematically generate guided wave dispersion curves of phase velocity $V_{ph}$ vs. fd and group velocity Vg vs. fd.

3. Select guided wave mode points on the dispersion curves, to determine the phase velocity and frequency, hence the wavelength $\lambda$. The choice depends on goals of an inspection of defect type and subsequent wave structure to optimally detect such a defect. Wave structure is calculated using elasticity and wave propagation theory.

4. Determine the spacing between the teeth of the comb transducer, and the teeth width as well.

5. Determine the geometry of the comb transducer.

Thus, in summary the present invention and this particular design allows the comb transducer concept to be extended to pipe and curved structures along with special design, fabrication and utilization aspects.

Figure 19:
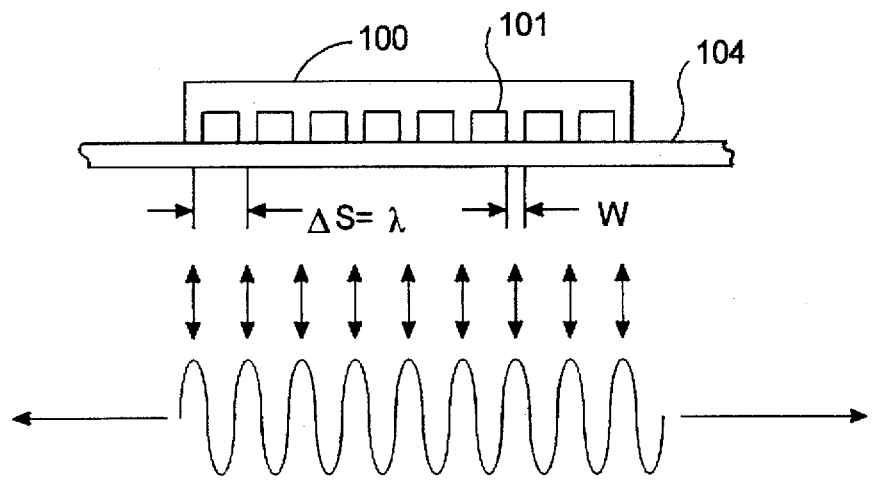
FIG. 19 is a simplified cross-sectional view showing a transducer mounted on the exterior wall of a tube and also illustrates the guided wave generated thereby.

FIG. 19 illustrates the comb transducer principle. The structure of the comb transducer 100 consists of a group of equally spaced parallel elements 101 (teeth or legs) in the front face. The physical principle of the comb transducer is the periodical vibration of each tooth in phase at the same frequency to generate guided waves of the wavelength, $\lambda$, equal to the spacing, $\Delta S$, with the vibration frequency, f. The guided waves include waves propagating along plates, waves propagating along tube walls, called tube waves, and waves propagating along pipe walls, called pipe waves, and waves propagating along material surfaces, called surface waves. The guided waves generated with a comb transducer propagate in directions along which the transducer elements are arranged. The relationship between the comb transducer element spacing and the guided wave mode is derived as follows.

EQUATIONS

In a plate or a pipe, assuming the wave length is $\lambda$; the spacing between teeth is $\Delta S$; the frequency is f; d is thickness of the plate or pipe wall; and the guided wave phase velocity is $V_{ph}$. For a particular guided wave mode, the following relationship should be satisfied $$V_{ph}=f\lambda \text{ or } V_{ph}=\Delta S \cdot f \quad (1)$$

where $$K=\Delta S/d \quad (2)$$

$$X=fd \quad (3)$$

therefore $V_{ph}=Kfd=K \cdot X$:

in the dispersion curve, phase velocity is a function of fd:

$$V_{ph}=F(X) \quad (4)$$

Figure 20:
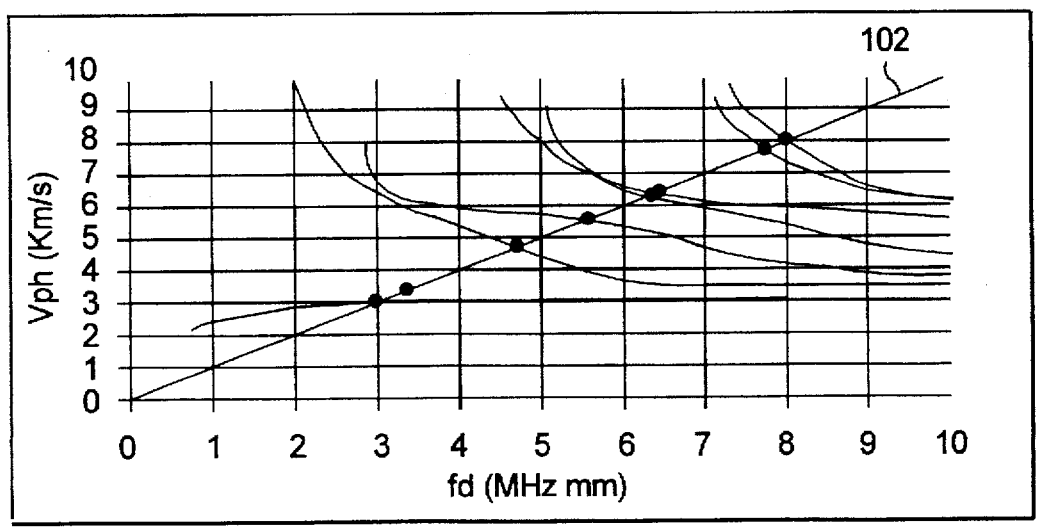
FIG. 20 is a set of phase velocity dispersion curves for a steel pipe and includes a straight line for particular comb transducer of fixed spacing ΔS.

Equation (1) can be graphically found to be a straight line 102 as shown in FIG. 20. Equation (4) is a group of phase velocity dispersion curves in FIG. 20. The solution of these two equations (1) and (4), can be graphically found to be the intersection points of the straight line 102 and the dispersion curves.

The spacing obtained for the comb transducer design is:

$$\Delta S = \lambda = V_{ph}/f \quad (5)$$

If spacing is changed, a new straight line can therefore by plotted in FIG. 20.

Figure 21:
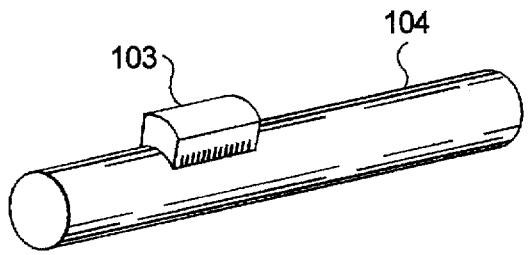
FIG. 21 illustrates a perspective view of one embodiment of a comb transducer affixed to a pipe.

FIG. 21 is an overview of a comb transducer 103 on a pipe 104 for inspection. The comb transducer can be designed with a flat front surface for plate inspection as illustrated in FIG. 19 and with a curved surface matching the tube or pipe surface curvature for tube or pipe inspection. The guided waves propagate in the tube or pipe wall along the tube or pipe axial direction for axisymmetric modes.

Figure 22A:
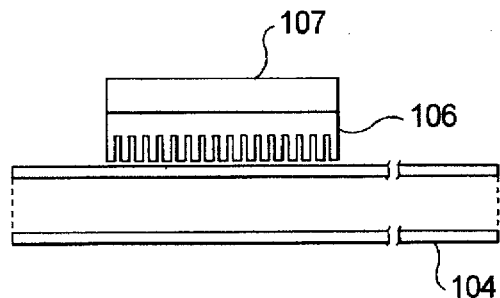
FIGS. 22A through 22D show possible configurations of the comb transducer of FIG. 21.
Figure 22B:
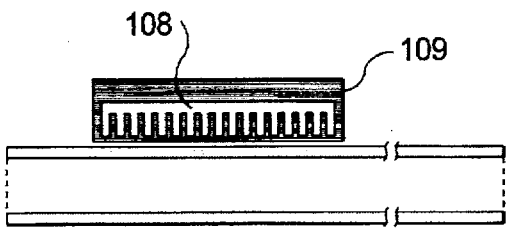
Figure 22C:
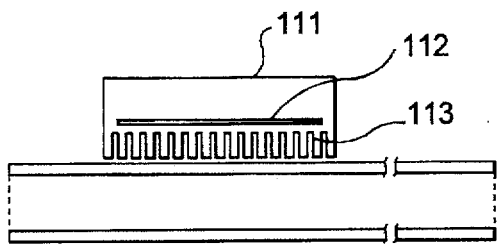
Figure 22D:
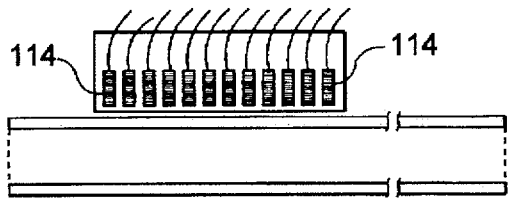

The comb transducer can be made in different ways. In FIG. 22A, a comb shoe 106 is attached to a normal beam transducer 107. In FIG. 22B, there is a piezoelectric comb 108 which is in a housing 109. Then, FIG. 22C is similar to FIG. 22B where there is a comb housing 111 but there is a piezoelectric plate 112 driving the comb 113 which is at the bottom of housing 111. Finally, in FIG. 22D this consists of a group of independent elements 114 which are equally spaced and arranged in parallel order and may be driven by an ultrasonic pulse/receiver which sends electrical pulses in phase to all elements to excite the guided waves similar to the other transducers of FIGS. 22A and 22B. But in FIG. 22D each element serves as an independent tooth.

The comb transducers shown in FIGS. 21, 22A, 22B, 22C and 22D cover a section of the circumference of the pipe. Therefore, they excite, generally, non-axisymmetric modes. These modes could have some applications. But they cause some difficulty in signal analysis unless non-axisymmetric phase propagation is thoroughly understood. This is important since refection from a defect is generally non-axisymmetric. In most practical situations, axisymmetric modes are recommended. One way of exciting the axisymmetric modes is to use a 360° comb transducer that consists of a group of circular transducers 116 that are equally spaced arranged in parallel in pipe axial direction as illustrated in FIGS. 23 and 24. Because of the even excitation around the circumference, only axisymmetric modes can be generated. The 360° comb transducer can be made in two ways as illustrated in FIGS. 25A, 25B, 25C, 26A, 26B and 26C that show the cross-section of the 360° comb transducer. FIG. 25A is the 360° comb transducer that consists of a group of single circular elements 117 which work together in phase. This type of transducer should generate uniform axisymmetric modes in the pipe. But it may be used only for pipes of one particular diameter. FIG. 26A shows the elements 118 of the 360° multiple array comb transducer. Each 360° element consists of a group of equally spaced normal beam transducers, called a transducer array. This type of transducer can be used on pipes of similar diameters by adjusting the normal beam transducer spacing.

Referring to the details of the one-piece transducer 117 in FIG. 25A, as illustrated in FIG. 25B, the pipe or tube 104 which is the inner diameter has overlaid on it a shoe 119 on which is, of course, the single transducer 117. Then, referring to FIG. 26B, there is a similar shoe 119' but affixed to it are individual transducers 118. Then, FIGS. 25C and 26C show axial cross-sections.

The generated guided wave in the pipe or plate may be received using three methods as illustrated in FIGS. 27A–27C. FIG. 27A is the pulse echo method: the comb transducer 120 serves as both sender and receiver; and the echo is received by the comb. FIG. 27B is the through transmission method using a comb transducer 121 to receive the signal. Both receive a particular selected wave mode because the comb transducers are designed for it. FIG. 27C is the through transmission method using an angle beam transducer 122 to receive the signal. This method is also very effective in receiving the particular excited mode because Snell's Law allows a particular mode conversion to a longitudinal wave that is received by the angle beam transducer. It is also possible to receive guided waves using a normal beam transducer directly contacted to the pipe or plate surface. But mode selectivity is not as good as above.

Figure 28:
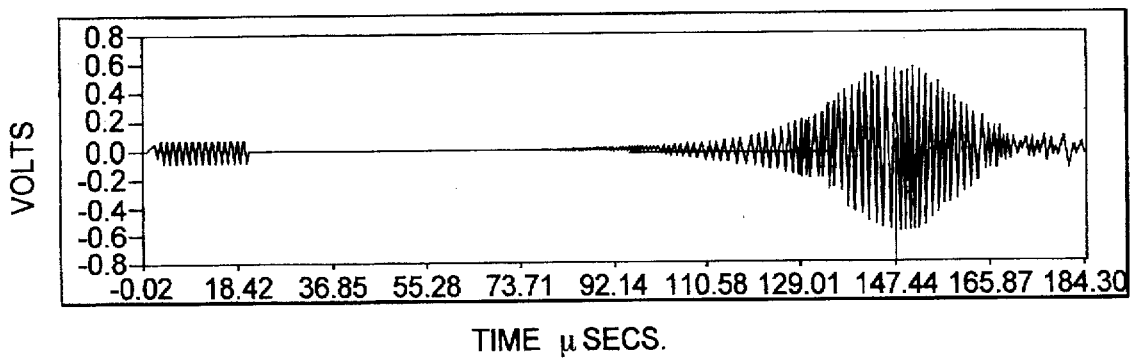
FIG. 28 illustrates a guided wave signal from a particular type of pipe.
Figure 29:
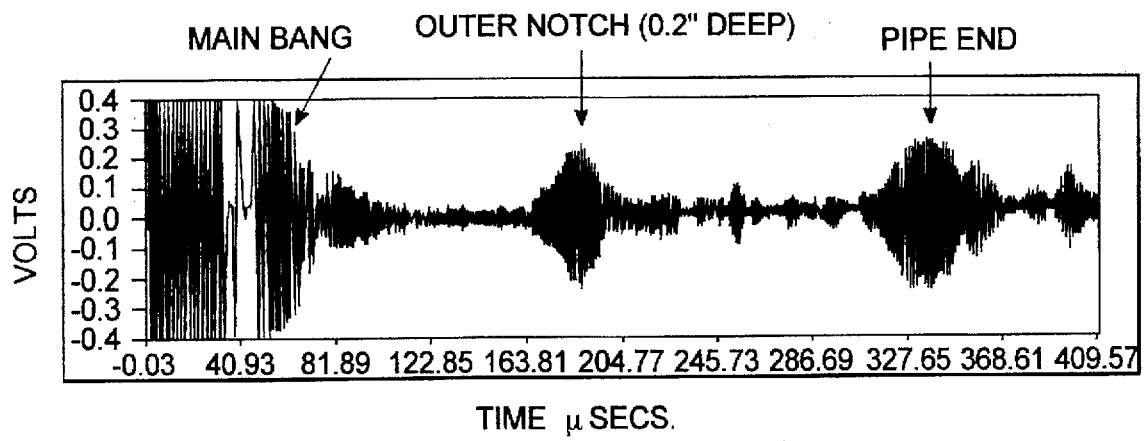
FIG. 29 illustrates a radio frequency signal in the same pipe as FIG. 28.

FIGS. 28 and 29 show the experimentally generated and received guided wave signals using the comb transducer technique.

FIG. 28 shows a guided wave signal from an outer 1" circumferential notch in a 6" diameter pipe using a 15 element comb transducer as a sender and an angle beam transducer of 34.2° as a receiver at a 12.0" distance between these two transducers. The experimental results: mode $S_l$, f=0.840 MGz, fd=6.13 MGz mm, Vph=4.80 Km/s, Vg=3.20 Km/s.

FIG. 29 is an RF signal from the outer notch in a 6" diameter pipe using a 15 element comb transducer for a pulse echo setup. The mode was proven to be all at frequency f=0.734 MGz. The left end signal is the excitation signal from the transducer and tone burst pulser; the middle signal is the echo from the outer notch 12" from the transducer, and the right signal is the echo from the pipe end 24" from the transducer.

Figure 30:
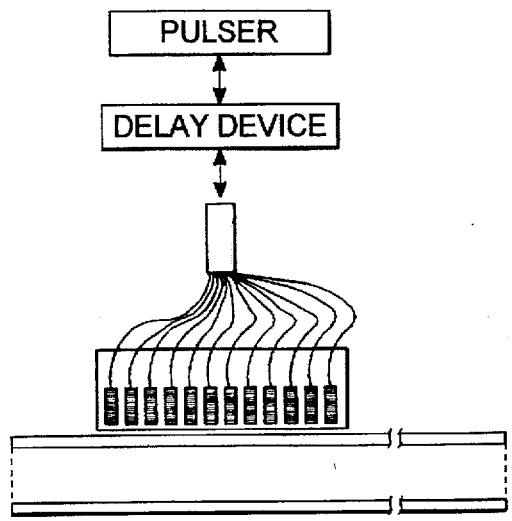
FIG. 30 illustrates a multiple element phase delay comb transducer.
Figure 31:
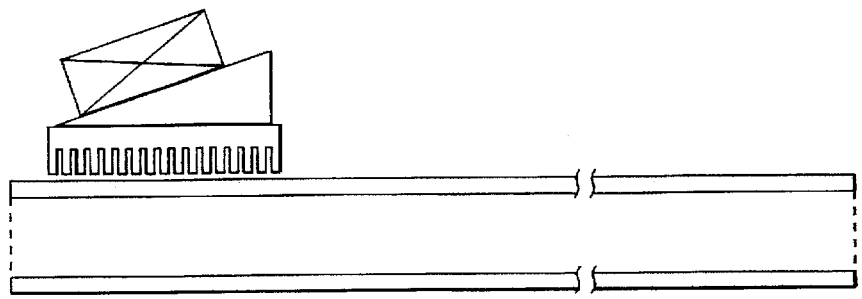
FIG. 31 illustrates an angle beam phase delay comb transducer.

The element spacing can be determined during the probe design. It can also be determined by adjusting the time delay of each element to set an "effective spacing", $\Delta S_e$ whose effect is the same as a comb transducer of spacing $\Delta S$. This time delay can be implemented with an electronic delay device or an angle beam incidence. FIG. 30 is a multiple element phase delay comb transducer. A pulser sends pulses to a delay device, which splits the pulse into channels of the same number of comb transducer elements; or the pulser sends multiple pulses of the same number of comb transducer elements to the delay device. Then, the delay device can adjust the phase of each pulse for a certain time delay. For example, an equal time delay can be set to all of the elements from the first to the last sequentially. Thus, an effective comb element spacing can be adjusted to generate the desired modes without changing the comb transducer physical spacing. FIG. 31 is an angle beam phase delay comb transducer. The time delay of each comb transducer element can be implemented by an angle beam transducer mounted on a comb shoe. The time delay can be adjusted by adjusting the angle.

In summary an improved method of using guided ultrasonic waves for inspection of defects is provided.

EQUATIONS $$det \begin{vmatrix} B_{11} & B_{12} & B_{13} & B_{14} & O \\ B_{21} & B_{22} & B_{23} & B_{24} & O \\ B_{31} & B_{32} & B_{33} & B_{34} & B_{35} \\ B_{41} & B_{42} & B_{43} & B_{44} & O \\ B_{51} & B_{52} & B_{53} & B_{54} & B_{55} \end{vmatrix} = O \quad (1)$$

$$B_{11} = -\{\lambda(k_1^2 + k^2) + 2Gk_1^2\}J_0(k_1a) + 2Gk_1\frac{J_1(k_1a)}{a}$$

-continued $$B_{12} = -\{\lambda(k_1^2+k^2)+2Gk_1^2\}Y_0(k_1a)+2Gk_1\frac{Y_1(k_1a)}{a}$$

$$B_{13} = \{2iGk\}\{k_1J_0(k_1a)-\frac{1}{a}J_1(k_1a)\}$$

$$B_{14} = \{2iGk\}\{k_1Y_0(k_1a)-\frac{1}{a}Y_1(k_1a)\}$$

$$B_{22}=\{2iGkk_1\}\{Y_1(k_1a)\}$$

$$B_{23}=G\{k^2-k_1^2\}\{J_1(k_1a)\}$$

$$B_{24}=G\{k^2-k_1^2\}\{Y_1(k_1a)\}$$

$$B_{31} = -\{\lambda(k_1^2)+K^2)+2Gk_1^2\}J_0(k_1b)+2Gk_1\frac{J_1(k_1b)}{b}$$

$$B_{32} = -\{\lambda(k_1^2+k^2)+2Gk_1^2\}Y_0(k_1b)+2Gk_1\frac{Y_1(k_1b)}{b}$$

$$B_{33} = \{2iGk\}\{k_1J_0(k_1b)-\frac{1}{b}J_1(k_1b)\}$$

$$B_{34} = \{2iGk\}\{k_1Y_0(k_1b)-\frac{1}{b}Y_1(k_1b)\}$$

$$B_{34}=\lambda[(k_w^2+k^2)H_0^{(2)}(k_wb)]$$

$$B_{41}=\{2iGkk_1\}\{J_1(k_1b)\}$$

$$B_{42}=\{2iGkk_1\}\{Y_1(k_1b)\}$$

$$B_{43}=G\{k^2-k_1^2\}\{J_1(k_1b)\}$$

$$B_{44}=G\{k^2-k_1^2\}\{Y_1(k_1b)\}$$

$$B_{51}=-k_1J_1(k_1b)$$

$$B_{52}=k_1Y_1(k_1b)$$

$$B_{53}=ikJ_1(k_1b)$$

$$B_{54}=ikY_1(k_1b)$$

$$B_{55}=k_wH_1^{(2)}(k_wb)$$

after obtaining the complex eigen values k, the phase velocity $C_{ph}$ and attenuation $\alpha$ can be calculated in the following manner.

$$C_{ph}=(1)/k_{real} \qquad (2)$$

$$\alpha=-k_{im}\rightarrow(dB=20\log\alpha) \qquad (3)$$

What is claimed is:

1. A system of using guided ultrasonic waves for inspection of defects in tubing using a transducer for generating the guided waves at any one of several parameters of phase velocity, $C_{ph}$ and frequency, f, to operate at a specific point on a dispersion curve of a specific ultrasonic guided wave mode within said tubing, said transducer being tuned to a said phase velocity, by:

providing as a part of said transducer an annular array of radiating elements substantially concentric with and spaced from each other along the same direction as the direction of propagation of said guided waves;

means for generating by said elements of said transducer a said guided wave of any selected one of said several parameters of phase velocity;

whereby the structure of said wave may be readily changed for effective detection, location analysis, classification, and sizing.

2. A system as in claim 1 including means for receiving reflections from a defect which are nonaxisymmetric by use of a said transducer in the shape of a conical receiver having segmented elements aligned in the same direction as said guided waves.

3. A system as in claim 1 where said transducer includes elements arranged in an array around the external circumference of said tubing.

4. A system as in claim 1 where said radiating elements extend either substantially around the total external circumference of said tubing to generate axisymmetric guided waves or are partially wrapped around to provide nonaxisymmetric guided waves.

5. A system as in claim 1 where said transducer is in the form of a flexible multi-element comb which is wrapped around said tubing.

6. A system as in claim 1 where said transducer is of the comb type with spaced radiators for placement on the external surface of said tubing to generate desired guide waves down said tubing for defect detection where each of said radiators extends substantially entirely around the external circumference of the tubing to generate axisymmetric guided waves.

7. A system as in claim 1 including a transducer for receiving nonaxisymmetric reflections in the form of a segmented comb around the circumference of said tubing.

8. A system as in claim 1 where said tubing is water loaded.

9. A system as in claim 1 where said means for generating by said elements of said transducer includes means for producing time delays from one element to the next to provide a guided wave having a phase velocity irrespective of spacing of said elements.

10. A system as in claim 9 where said transducer is formed by a comb type system of piezoelectric ultrasonic radiators with the spacing defined as width plus gap of the radiators which is normally proportional to phase velocity in the absence of superimposed time delayed signals.

11. A system as in claim 9 including a tone burst function generator is used to generate said frequency, said tone burst generator generating a burst of a predetermined number of cycles to control bandwidth.

12. A system as in claim 9 where said transducer is in the shape of a cone and said radiating elements are arranged as a conical annular array over said cone, said predetermined time delays providing phase velocity tuning.

13. A system as in claim 9 where said means for generating includes a time delayed laser beam to produce a particular loading pattern on the inside of said tubing to provide a said specific phase velocity.

* * * * *

UNITED STATES PATENT AND TRADEMARK OFFICE
CERTIFICATE OF CORRECTION

PATENT NO. : 5,734,588
DATED : March 31, 1998
INVENTOR(S) : ROSE, et al.

It is certified that error appears in the above-identified patent and that said Letters Patent is hereby corrected as shown below:

On the title page, after "[73] Assignee:" please delete "Electric Power Research Institute Inc., Palo Alto, Calif." and insert therefor --The Penn State Research Foundation, University Park, Pennsylvania--.

Signed and Sealed this

Twenty-third Day of March, 1999

Attest:

Q. TODD DICKINSON

*Attesting Officer*     *Acting Commissioner of Patents and Trademarks*